(12) United States Patent
Hsia

(10) Patent No.: US 10,653,733 B2
(45) Date of Patent: *May 19, 2020

(54) NUTRITIONAL COMPOSITION

(71) Applicant: Houn Simon Hsia, Irvine, CA (US)

(72) Inventor: Houn Simon Hsia, Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/156,990

(22) Filed: Oct. 10, 2018

(65) Prior Publication Data

US 2019/0038687 A1 Feb. 7, 2019

Related U.S. Application Data

(60) Continuation of application No. 15/205,786, filed on Jul. 8, 2016, now Pat. No. 10,117,902, which is a division of application No. 13/852,472, filed on Mar. 28, 2013, now abandoned.

(51) Int. Cl.

| | | |
|---|---|---|
| *A61K 36/064* | (2006.01) | |
| *A61K 36/06* | (2006.01) | |
| *A61K 35/60* | (2006.01) | |
| *A61K 31/05* | (2006.01) | |
| *A61K 31/593* | (2006.01) | |
| *A61K 31/122* | (2006.01) | |
| *A61K 31/4415* | (2006.01) | |
| *A61K 33/30* | (2006.01) | |
| *A61K 33/24* | (2019.01) | |
| *A61K 31/198* | (2006.01) | |
| *A61K 31/202* | (2006.01) | |
| *A61K 31/18* | (2006.01) | |
| *A61K 31/24* | (2006.01) | |
| *A61K 31/30* | (2006.01) | |
| *A61K 31/32* | (2006.01) | |
| *A61K 31/34* | (2006.01) | |
| *A61K 31/519* | (2006.01) | |
| *A61K 33/18* | (2006.01) | |
| *A61K 33/32* | (2006.01) | |
| *A61K 33/34* | (2006.01) | |
| *A23L 33/105* | (2016.01) | |
| *A23L 33/115* | (2016.01) | |
| *A23L 33/14* | (2016.01) | |
| *A23L 33/15* | (2016.01) | |
| *A23L 33/155* | (2016.01) | |
| *A23L 33/16* | (2016.01) | |
| *A23L 33/175* | (2016.01) | |
| *A61K 31/015* | (2006.01) | |

(52) U.S. Cl.
CPC .......... *A61K 36/064* (2013.01); *A23L 33/105* (2016.08); *A23L 33/115* (2016.08); *A23L 33/14* (2016.08); *A23L 33/15* (2016.08); *A23L 33/155* (2016.08); *A23L 33/16* (2016.08); *A23L 33/175* (2016.08); *A61K 31/015* (2013.01); *A61K 31/05* (2013.01); *A61K 31/122* (2013.01); *A61K 31/18* (2013.01); *A61K 31/198* (2013.01); *A61K 31/202* (2013.01); *A61K 31/24* (2013.01); *A61K 31/30* (2013.01); *A61K 31/32* (2013.01); *A61K 31/34* (2013.01); *A61K 31/4415* (2013.01); *A61K 31/519* (2013.01); *A61K 31/593* (2013.01); *A61K 33/18* (2013.01); *A61K 33/24* (2013.01); *A61K 33/30* (2013.01); *A61K 33/32* (2013.01); *A61K 33/34* (2013.01); *A61K 35/60* (2013.01); *A61K 36/06* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,976,548 | A | * 11/1999 | Hsia | A23L 2/385 424/439 |
| 6,197,295 | B1 | 3/2001 | Hsia et al. | |
| 6,440,464 | B1 | 8/2002 | Hsia et al. | |
| 6,605,296 | B1 | 8/2003 | Stuckler | |
| 6,620,440 | B1 | 9/2003 | Hsia et al. | |
| 8,017,147 | B2 * | 9/2011 | Mazed | A61K 36/02 424/450 |
| 2006/0275506 | A1 * | 12/2006 | Fisher | A23L 2/52 424/641 |

FOREIGN PATENT DOCUMENTS

| | | |
|---|---|---|
| WO | 0007607 | 2/2000 |
| WO | 2012122295 | 9/2012 |

OTHER PUBLICATIONS

Ben-Amotz et al., Bioavailability of a natural isomer mixture compared with synthetic all-trans beta-carotene in human serum, 1996, the American Journal of Clinical Nutrition 65(5): 729-734.

* cited by examiner

*Primary Examiner* — Robert J Yamasaki
(74) *Attorney, Agent, or Firm* — Fish IP Law, LLP

(57) ABSTRACT

The present invention provides nutritional compositions that are employed as oral supplementation to the human diet. The compositions of the present invention provide for supplementation to the diet of the cancer patient, as well as preventative dietary supplementation aimed at supporting the human immune system for those not currently suffering from cancer. The present invention is comprised of specific combinations of selected forms of unique sets of certain vitamins, minerals, protein, carbohydrates and phytochemicals.

16 Claims, No Drawings

NUTRITIONAL COMPOSITION

This application is a continuation of U.S. patent application Ser. No. 15/205,786, filed on Jul. 8, 2016, which is a divisional application of U.S. patent application Ser. No. 13/852,472, filed Mar. 28, 2013. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The present invention relates to nutritional compositions useful for increasing the efficacy of cancer therapies, including chemotherapy, radiation and target therapies; and more specifically to nutritional compositions to promote anti-tumor activity.

BACKGROUND

The following description includes information that may be useful in understanding the present invention. It is not an admission that any of the information provided herein is prior art or relevant to the presently claimed invention, or that any publication specifically or implicitly referenced is prior art.

Cancer is one of the most deadly diseases of all mankind. Preventing and treatment of cancer is, therefore, and extremely important endeavor for mankind to pursue. Much progress has been made over the last 50 years for the treatment of cancer, including chemotherapeutic, radiation and most recently, target therapies. A major shortcoming of these therapeutic treatments is their harmful effects to the human system since, in many cases, the practice of such therapies causes severe weight loss, hair loss, and in many cases, death.

It is believed that one of the major causes of the ill-effects of cancer therapies is that they tax the human immune system. A healthy and potent human immune system is very important to combat the ill-effects of the cancer therapies. The present invention overcomes the shortcomings of the art of cancer therapy by providing compositions that work together to enhance the immune system such that the health of the cancer patient is not compromised by the harsh effects of the cancer therapies, and as a result, can overcome such effects, resulting in more efficient cancer remedial therapeutic treatments.

SUMMARY OF THE INVENTION

The present invention provides nutritional compositions that are employed as oral supplementation to the human diet. The compositions of the present invention provide for supplementation to the diet of the cancer patient, as well as preventative dietary supplementation aimed at supporting the human immune system for those not currently suffering from cancer.

It is a prime objective of the present invention to provide nutritive compositions that when used in combination with radiation, target or chemotherapy, provide for an increased activity in combating neoplastic growth.

It is another objective of the present invention to provide for anti-neoplastic effects by dietary supplementation utilizing specific forms of nutrients such as selenium yeast and fish oil.

It is another objective of the present invention to provide for compositions that help prevent cancer.

DETAILED DESCRIPTION

The present invention teaches a combination of specific nutrients suitable for oral consumption by the human body. The compositions of the present invention when orally ingested on a daily basis, in combination with or without therapeutic treatments for cancer, specifically chemotherapy, target therapy and radiation therapy, work in a synergistic fashion together to aid the cancer patient in eliminating the cancer, healing of the cancer and recovery from the cancer. The compositions of the present invention may also be ingested on a daily, or periodic basis to help prevent cancer.

Although the mechanism of action of the compositions of the present invention are not well understood, many cases have been reported of cancer patients benefiting from the use of the present invention in combination with the therapeutic treatments for cancer. It is believed that the key ingredients of the present invention work synergistically together to aid in the anti-neoplastic processes. The recent publication entitled "Reduction of Splenic Immunosuppressive Cells and Enhancement of Anti-Tumor Immunity by Synergy of Fish Oil and Selenium Yeast" (Wang h, Chan Y-L, et al. (2013) PLoS ONE 8(1):e52912. Dol: I 0.1371/journal.pone.005912) provides evidence that indeed the compositions of the present invention provide said synergistic action, and also that the compositions taught by the present invention are novel and useful for the prevention and treatment of cancer.

These compositions include as preferred embodiment selenium. The preferred form of selenium is selenium yeast. The preferred amount of selenium yeast is from about 5 mcg to about 500 mcg, and more preferred between about 10 mcg to about 250 mcg, and most preferably from between 25 mcg to about 150 mcg. The preferred selenium yeast are *Saccharomyces cerevisiae, Saccharomyces exiguous, Saccharomyces pastorianus, Saccharomyces boulardii, Saccharomyces bayanus, Saccharomyces eubayanus, Saccharomyces florentinus, Saccharomyces fragilis.*

Another essential ingredient of the present invention is fish oil. The preferred fish oil has an EDA/DHA ratio of from between 1 part EPA to about 5 parts DHA, and from between 5 parts EPA to 1 part DHA, and more preferably from about 2 parts EPA to 1 part DHA, and most preferably from about 3 parts EPA to about 2 parts DHA. The EPAIDHA content of the fish oil preparations of the present invention are from between 10% to about 90%, more preferably from between 30% to about 70% and most preferably from about 40% to about 60%. The preferred amounts of fish oil EPAIDHA preparation of the present invention is from 0.50 mg to about 1.5 g, and more preferably between 250 mg to about 1000 mg, and most preferably between 350 mg to about 750 mg.

Another essential component of the present invention is Beta Carotene. The preferred form of beta carotene is the naturally occurring form. The preferred amount is between 500 iu and 10,000 iu, and more preferably between 1500 iu and 7500 iu, and most preferably between about 1000 iu and 3000 iu.

Resverotrol is another important nutrient of the present invention. The preferred form of Resverotrol is from plan extract. The preferred amount of Resverotrol in the extract is from between 50% to about 98%, and most preferably about 95%. The preferred amount of Resverotrol extract to be employed in the present invention is from about 5 mg to about 1500 mg, and more preferably from about 50 mg to about 300 mg, and most preferably from about 75 mg to about 150 mg.

Additionally, Vitamin D3 may be added to the nutritional compositions of the present invention. The preferred form of Vitamin D3 is Cholecalciferol. The preferred amount of Vitamin D3 is from between 50 iu and 3000 iu, and more preferably between from about 70 iu to about 500 iu, and most preferably from about 100 iu to about 250 iu.

Another prime nutrient that may be included in the embodiments of the present invention is Vitamin K. The preferred form of Vitamin K is Phytonadione. The preferred amount of Vitamin K is between 2.5 mcg to about 250 mcg, more preferably from between 15 mcg to about 100 mcg, and most preferably between 20 mcg to about 75 mcg.

Another nutrient important to the efficacy of the present invention is Vitamin B6. The preferred form of Vitamin B6 is Pyridoxine hydrochloride. The preferred amount is between 0.1 mg to about 100 mg, most preferably between about 0.5 mg to about 25 mg, and most preferably from about 0.75 mg to about 10 mg.

Additionally, Vitamin B12 may be included in the present invention. The preferred form of Vitamin B12 is Cyanocobalamin. The preferred amount of Vitamin B12 is between about 0.3 mcg to about 900 mcg, most preferably between about 0.75 mcg to about 50 mcg, and most preferably between 1 mcg and 10 mcg.

Another nutrient that is important to the present invention is Folic Acid. The preferred amount of Folic Acid is between about 25 mcg to about 1000 mcg, most preferably between about 100 mcg to about 750 mcg, and most preferably between 200 mcg and 400 mcg.

The mineral Zinc is important to include in the present invention. The preferred amount of Zinc is between about 0.65 mcg to about 4000 mcg, most preferably between about 1 mcg to about 400 mcg, and most preferably between 3 mcg and 50 mcg.

The mineral Chromium is important to include in the present invention. The preferred form of Chromium is from yeast. The preferred amount of Chromium is between about 30 mcg to about 3000 mcg, most preferably between about 50 mcg to about 500 mcg, and most preferably between 25 mcg and 100 mcg.

The mineral Molybdenum is important to include in the present invention. The preferred form of Molybdenum is from yeast. The preferred amount of Molybdenum is between about 2.5 mcg to about 1000 mcg, most preferably between about 10 mcg to about 130 mcg, and most preferably between 15 mcg and 60 mcg.

The amino acid glutamine is important to include in the present invention. The preferred amount of glutamine is between about 2.1 g to about 250 g, most preferably between about 11 g to about 135 g, and most preferably between 10 g and 50 g.

The amino acid arginine is important to include in the present invention. The preferred amount of arginine is between about 0.71 g to about 25 g, most preferably between about 3.0 g to about 15 g, and most preferably between 5 g and 13 g.

The amino acid taurine is important to include in the present invention. The preferred amount of taurine is between about 1.1 g to about 29 g, most preferably between about 2.3 g to about 15 g, and most preferably between 3 g and 11 g.

The amino acid lysine is important to include in the present invention. The preferred amount of taurine is between about 0.81 g to about 49 g, most preferably between about 5.3 g to about 35 g, and most preferably between 6 g and 18 g.

Another important nutrient is Coenzyme Q-10. The preferred amount of Coenzyme Q-10 is from about 30 mg to about 1000 mg, most preferably from between about 50 mg to 300 mg, and most preferably between about 60 mg to about 180 mg.

The following examples are illustrative only and do not limit the invention in any fashion.

Example 1

| Ingredient | Amount |
| --- | --- |
| Fish Oil | 70 mg |
| Selenium (from Selenium yeast) | 2500 mcg |
| Beta Carotene | 1000 iu |
| Vitamin D3 | 100 iu |
| Vitamin K | 15 mcg |
| Vitamin B6 | 0.5 mg |
| Vitamin B12 | 1 mcg |
| Folic Acid | 250 mcg |
| Zinc | 5.0 mg |
| Chromium | 25 mcg |
| Molybdenum | 15 mcg |
| Glutamine | 20 g |
| Arginine | 5.1 g |
| Taurine | 3.2 g |
| Lysine | 7.3 g |
| CoQ-10 | 50 mg |
| Niacin | 2.1 mg |
| Riboflavin | 600 mcg |
| Thiamin | 530 mcg |
| Biotin | 2 mg |
| Calcium | 200 mg |
| Iron | 3 mg |
| Phosphorous | 213 mg |
| Iodine | 35 mg |
| Copper | 500 mcg |
| Manganese | 570 mcg |
| Inositol | 1.2 g |
| Sucrose | 3.5 g |
| Whey Protein Isolate | 0.75 g |
| Non-Fat Milk | 0.2 g |
| Rice Protein | 0.23 g |
| Calcium Caseinate | 0.14 g |
| Soy Lecithin | 0.1 g |

The above ingredients were admixed and shaken until homogeneous blend was obtained. The blended composition was poured into 250 mL of water, mixed and then consumed via drinking.

Example 2

| Ingredient | Amount |
| --- | --- |
| Fish Oil | 70 mg |
| Selenium (from Selenium yeast) | 2500 mcg |
| Beta Carotene | 1000 iu |
| Vitamin D3 | 100 iu |
| Vitamin K | 15 mcg |
| Vitamin B6 | 0.5 mg |
| Vitamin B12 | 1 mcg |
| Folic Acid | 250 mcg |
| Iron | 3 mg |
| Phosphorous | 213 mg |
| Iodine | 35 mg |
| Copper | 500 mcg |
| Manganese | 570 mcg |
| Inositol | 1.2 g |
| Sucrose | 3.5 g |
| Whey Protein Isolate | 0.75 g |
| Non-Fat Milk | 0.2 g |

| Ingredient | Amount |
| --- | --- |
| Rice Protein | 0.23 g |
| Calcium Caseinate | 0.14 g |
| Soy Lecithin | 0.1 g |

The above ingredients were admixed and shaken until homogeneous blend was obtained. The blended composition was poured into 250 mL of water, mixed and then consumed via drinking.

Example 3

| Ingredient | Amount |
| --- | --- |
| Fish Oil | 90 mg |
| Selenium (from Selenium yeast) | 2540 mcg |
| Beta Carotene | 1300 iu |
| Vitamin D3 | 80 iu |
| Vitamin K | 15 mcg |
| Vitamin B6 | 0.5 mg |
| Vitamin B12 | 1 mcg |
| Folic Acid | 250 mcg |
| Zinc | 3.0 mg |
| Chromium | 25 mcg |
| Molybdenum | 25 mcg |
| Glutamine | 29 g |
| Arginine | 7.1 g |
| Taurine | 3.2 g |
| Lysine | 7.6 g |
| CoQ-10 | 100 mg |
| Manganese | 570 mcg |
| Inositol | 2.7 g |
| Sucrose | 3.5 g |
| Whey Protein Isolate | 0.75 g |
| Non-Fat Milk | 0.2 g |
| Rice Protein | 0.23 g |
| Calcium Caseinate | 0.14 g |
| Soy Lecithin | 0.1 g |

The above ingredients were admixed and shaken until homogeneous blend was obtained. The blended composition was poured into 250 mL of water, mixed and then consumed via drinking.

Example 4

| Ingredient | Amount |
| --- | --- |
| Fish Oil | 110 mg |
| Selenium (from Selenium yeast) | 1500 mcg |
| Beta Carotene | 200 iu |
| Vitamin D3 | 100 iu |
| Vitamin K | 15 mcg |
| Vitamin B6 | 0.5 mg |
| Vitamin B12 | 1 mcg |
| Folic Acid | 250 mcg |
| Zinc | 5.0 mg |
| Chromium | 25 mcg |
| Molybdenum | 15 mcg |
| Glutamine | 20 g |
| Arginine | 5.1 g |
| Taurine | 3.2 g |
| Lysine | 7.3 g |
| CoQ-10 | 50 mg |
| Niacin | 2.1 mg |
| Riboflavin | 600 mcg |
| Thiamin | 530 mcg |
| Biotin | 2 mg |
| Calcium | 200 mg |
| Iron | 3 mg |
| Phosphorous | 213 mg |
| Iodine | 35 mg |
| Copper | 500 mcg |
| Manganese | 570 mcg |
| Inositol | 1.2 g |
| Sucrose | 3.5 g |
| Whey Protein Isolate | 0.75 g |
| Non-Fat Milk | 0.2 g |
| Rice Protein | 0.23 g |
| Calcium Caseinate | 0.14 g |
| Soy Lecithin | 0.1 g |

The above ingredients were admixed and shaken until homogeneous blend was obtained. The blended composition was poured into 250 mL of water, mixed and then consumed via drinking.

Example 5

| Ingredient | Amount |
| --- | --- |
| Fish Oil | 90 mg |
| Selenium (from Selenium yeast) | 1560 mcg |
| Beta Carotene | 900 iu |
| Vitamin D3 | 92 iu |
| Vitamin K | 23 mcg |
| Vitamin B6 | 5.5 mg |
| Vitamin B12 | 3 mcg |
| Folic Acid | 250 mcg |
| Zinc | 6.0 mg |
| Chromium | 25 mcg |
| Molybdenum | 15 mcg |
| Glutamine | 23 g |
| Arginine | 5.1 g |
| Taurine | 2.2 g |
| Lysine | 7.3 g |
| CoQ-10 | 50 mg |
| Niacin | 2.1 mg |
| Riboflavin | 600 mcg |
| Thiamin | 530 mcg |
| Biotin | 2 mg |
| Calcium | 200 mg |
| Iron | 3 mg |
| Phosphorous | 213 mg |
| Iodine | 35 mg |
| Copper | 500 mcg |
| Manganese | 570 mcg |
| Inositol | 1.2 g |
| Sucrose | 3.5 g |
| Whey Protein Isolate | 0.75 g |
| Non-Fat Milk | 0.2 g |
| Rice Protein | 0.23 g |
| Calcium Caseinate | 0.14 g |
| Soy Lecithin | 0.1 g |

The above ingredients were admixed and shaken until homogeneous blend was obtained. The blended composition was poured into 250 mL of water, mixed and then consumed via drinking.

Example 6

| Ingredient | Amount |
| --- | --- |
| Fish Oil | 70 mg |
| Selenium (from Selenium yeast) | 2500 mcg |
| Beta Carotene | 1000 iu |

-continued

| Ingredient | Amount |
| --- | --- |
| Vitamin D3 | 100 iu |
| Vitamin K | 15 mcg |
| Vitamin B6 | 0.5 mg |
| Vitamin B12 | 1 mcg |
| Folic Acid | 250 mcg |
| Zinc | 5.0 mg |
| Chromium | 25 mcg |
| Molybdenum | 15 mcg |
| Glutamine | 20 g |
| Arginine | 5.1 g |
| Taurine | 3.2 g |
| Lysine | 7.3 g |
| CoQ-10 | 50 mg |
| Biotin | 2 mg |
| Calcium | 200 mg |
| Iron | 3 mg |
| Phosphorous | 213 mg |
| Iodine | 35 mg |
| Copper | 500 mcg |
| Manganese | 570 mcg |
| Inositol | 1.2 g |
| Sucrose | 3.5 g |
| Whey Protein Isolate | 0.75 g |
| Rice Protein | 0.23 g |
| Calcium Caseinate | 0.14 g |
| Soy Lecithin | 0.1 g |

The above ingredients were admixed and shaken until homogeneous blend was obtained. The blended composition was poured into 250 mL of water, mixed and then consumed via drinking.

What is claimed is:

1. An orally administrable nutritional composition effective for both reducing cachectic symptoms and suppressing neoplastic growth in a cancer patient, comprising:
   5 μg to 500 μg selenium yeast;
   0.5 mg to 1.5 g fish oil, the fish oil having a combined EPA/DHA content of between 10% to 90% and an EPA/DHA ratio of between 1:5 and 5:1;
   500 iu to 10,000 iu beta carotene;
   5 g to 13 g arginine;
   10 g to 50 g glutamine;
   6 g to 18 g lysine;
   milk protein;
   rice protein; and
   inositol.

2. The nutritional composition of claim 1, wherein the selenium yeast is in an amount from 10 μg to 250 μg.

3. The nutritional composition of claim 1, wherein the selenium yeast is in an amount from 25 μg to 150 μg.

4. The nutritional composition of claim 1, wherein the selenium yeast is one or more of the group consisting of: *Saccharomyces cerevisiae, Saccharomyces exiguous, Saccharomyces pastorianus, Saccharomyces boulardii, Saccharomyces bayanus, Saccharomyces eubayanus, Saccharomyces florentinus*, and *Saccharomyces fragilis*.

5. The nutritional composition of claim 1, wherein the fish oil has an EPA/DHA content of between 30% to 70%.

6. The nutritional composition of claim 1, wherein the fish oil has an EPA/DHA content of between 40% to 60%.

7. The nutritional composition of claim 1, wherein the fish oil has an EPA/DHA ratio of about 2:1.

8. The nutritional composition of claim 1, wherein the fish oil has an EPA/DHA ratio of about 3:2.

9. The nutritional composition of claim 1, wherein the beta carotene is in an amount between 1500 iu and 7500 iu.

10. The nutritional composition of claim 1, wherein the beta carotene is in an amount between 1000 iu and 3000 iu.

11. The nutritional composition of claim 1, wherein the nutritional composition additionally comprises 5 mg to 1500 mg resveratrol-containing extract, the resveratrol containing extract comprising between 50% and 98% resveratrol.

12. The nutritional composition of claim 1, wherein the nutritional composition additionally comprises one or more vitamins, the one or more vitamins selected from the group of: between 50 iu and 3000 iu vitamin D3, between 2.5 μg to 250 μg vitamin K, between 0.1 mg to 100 mg vitamin B6, and between 0.3 μg to 900 μg vitamin B12.

13. The nutritional composition of claim 1, wherein the nutritional composition additionally comprises between 25 μg to 1000 μg folic acid.

14. The nutritional composition of claim 1, wherein the nutritional composition additionally comprises one or more minerals, the one or more minerals being selected from the group of: between 0.65 μg to 4000 μg zinc, and between 50 μg to 500 μg chromium between 2.5 μg to 1000 μg molybdenum.

15. The nutritional composition of claim 1, wherein the nutritional composition additionally comprises between 30 mg to 1000 mg coenzyme Q-10.

16. The nutritional composition of claim 1, wherein the milk protein is selected from the group consisting of whey protein, casein, and non-fat milk.

* * * * *